(12) United States Patent
Chodosh et al.

(10) Patent No.: US 10,939,993 B2
(45) Date of Patent: Mar. 9, 2021

(54) KERATOPROSTHESIS APPARATUSES, SYSTEMS, AND METHODS

(71) Applicant: Massachusetts Eye and Ear Infirmary, Boston, MA (US)

(72) Inventors: James Chodosh, Boston, MA (US); Eleftherios Paschalis Ilios, Quincy, MA (US); John Graney, Wilmington, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 176 days.

(21) Appl. No.: 16/091,672

(22) PCT Filed: Apr. 7, 2017

(86) PCT No.: PCT/US2017/026612
§ 371 (c)(1),
(2) Date: Oct. 5, 2018

(87) PCT Pub. No.: WO2017/177145
PCT Pub. Date: Oct. 12, 2017

(65) Prior Publication Data
US 2019/0151077 A1 May 23, 2019

Related U.S. Application Data

(60) Provisional application No. 62/320,178, filed on Apr. 8, 2016.

(51) Int. Cl.
*A61F 2/14* (2006.01)

(52) U.S. Cl.
CPC ............... *A61F 2/15* (2015.04); *A61F 2/142* (2013.01); *A61F 2/145* (2013.01); *A61F 2/1451* (2015.04);
(Continued)

(58) Field of Classification Search
CPC ........ A61F 2/142; A61F 2/145; A61F 2/1451; A61F 2/1453; A61F 2/15
See application file for complete search history.

(56) References Cited

U.S. PATENT DOCUMENTS

| 4,315,337 A | 2/1982 | Choyce |
| 4,402,579 A * | 9/1983 | Poler .................. A61F 2/16 351/159.02 |

(Continued)

FOREIGN PATENT DOCUMENTS

| CN | 201029958 | 3/2008 |
| CN | 102283720 | 12/2011 |

(Continued)

OTHER PUBLICATIONS

CN Office Action in Chinese Appln. No. 201780028336.0, dated Apr. 20, 2020, 22 pages (with English translation).

(Continued)

*Primary Examiner* — David H Willse
*Assistant Examiner* — Javier G Blanco
(74) *Attorney, Agent, or Firm* — Fish & Richardson P.C.

(57) ABSTRACT

The present disclosure relates to keratoprosthesis apparatuses and methods of manufacturing keratoprosthesis apparatuses. The keratoprosthesis apparatus includes a circular backplate including a central aperture extending through the backplate from a face of the backplate to a posterior surface of the backplate. The circular backplate has a dome shape and comprises a plurality of spaced apart elongated slits extending radially outwardly from a central portion of the backplate. The plurality of spaced apart elongated slits surround the central aperture and extending through the backplate from the face of the backplate to the posterior of the backplate.

16 Claims, 4 Drawing Sheets

(52) U.S. Cl.
CPC ......... *A61F 2/1453* (2015.04); *A61F 2240/00* (2013.01); *A61F 2250/0025* (2013.01)

(56) References Cited

U.S. PATENT DOCUMENTS

| | | | |
|---|---|---|---|
| 4,624,669 | A | 11/1986 | Grendahl |
| 8,506,626 | B2 | 8/2013 | Azar et al. |
| 2006/0271026 | A1 | 11/2006 | Silvestrini et al. |
| 2008/0255663 | A1* | 10/2008 | Akpek .................... A61F 2/142 623/5.14 |
| 2010/0168849 | A1 | 7/2010 | Azar et al. |
| 2011/0160851 | A1 | 6/2011 | Mueller-Lierheim |
| 2012/0123361 | A1 | 5/2012 | Johansson et al. |
| 2014/0264981 | A1 | 9/2014 | Reboul et al. |
| 2015/0018949 | A1 | 1/2015 | Restrepo et al. |
| 2015/0216651 | A1 | 8/2015 | Parel et al. |

FOREIGN PATENT DOCUMENTS

| | | | |
|---|---|---|---|
| CN | 103260551 | 8/2013 | |
| WO | WO-2014039495 A1 * | 3/2014 | ............. A61F 2/142 |

OTHER PUBLICATIONS

International Preliminary Report on Patentability in International Application No. PCT/US2017/026612, dated Oct. 9, 2018, 8 pages.

International Search Report and Written Opinion in International Application No. PCT/US2017/026612, dated Jun. 19, 2017, 12 pages.

Paschalis et al., "In vitro and in vivo assessment of titanium surface modification for coloring the backplate of the Boston keratoprosthesis," Invest Ophthalmol Vis Sci, Jun. 2013, 54: 3863-3873.

Zerbe et al., "Results from the Multicenter Boston Type 1 Keratoprosthesis Study," Ophthalmology, 2006, 113:1779.e1-1779.e7.

Zhou et al., "The Role of Titanium Surface Microtopography on Adhesion, Proliferation, Transformation, and Matrix Deposition of Corneal Cells," IOVS, 2016, 57: 1-12.

IN Office Action in Indian Appln. No. 201817038153, dated Aug. 27, 2020, 10 pages.

* cited by examiner

KERATOPROSTHESIS APPARATUSES, SYSTEMS, AND METHODS

RELATED APPLICATION

The present application is a 371 U.S. National Phase Application of PCT/US2017/026612, filed on Apr. 7, 2017, which claims priority to U.S. Provisional Patent Application No. 62/320,178, filed on Apr. 8, 2016, entitled "KERATOPROSTHESIS APPARATUSES, SYSTEMS, AND METHODS," which application is incorporated herein by reference in its entirety.

TECHNICAL FIELD

The present application relates generally to the field of keratoprosthesis systems.

BACKGROUND

The front transparent part of the eye covering the iris and pupil is the cornea. A damaged or diseased cornea can impair vision and cause blindness. Patient that have a damaged or diseased cornea may require keratoplasty or surgery to their cornea. In some instances the corneal surgery may include replacement of all or a part of the cornea through a corneal transplantation. The corneal replacement can include implanting an artificial cornea or keratoprosthesis. A keratoprosthesis can be manufactured by precision machining, for example through formation on a lathe. The keratoprosthesis may include holes formed in a back plate portion of the keratoprosthesis to permit nutritious fluids to pass through the backplate to a grafted portion of the keratoprosthesis, namely a corneal graft. While these holes advantageously permit fluid permutation, they convey a look that is distinct from the eye and that emphasizes the presence of the implant.

SUMMARY

The inventors have appreciated that various embodiments disclosed herein provide keratoprosthesis apparatuses, systems, and methods.

Various embodiments provide a keratoprosthesis apparatuses. The keratoprosthesis apparatus includes a circular backplate including a central aperture extending through the backplate from a face of the backplate to a posterior surface of the backplate. The circular backplate has a dome shape and comprises a plurality of spaced apart elongated slits extending radially outwardly from a central portion of the backplate. The plurality of spaced apart elongated slits surround the central aperture and extending through the backplate from the face of the backplate to the posterior of the backplate.

In some embodiments, a slit in the plurality of elongated slits widens along a respective longitudinal axis from the central portion of the backplate, to an outer circumferential edge of the circular backplate.

In some embodiments, the circular backplate is composed of titanium.

In some embodiments, the posterior surface has a greater roughness than the face.

In some embodiments, the face is polished.

Various embodiments provide a method of manufacturing a keratoprosthesis apparatus. The methods include forming a central aperture through a circular backplate sheet to extend through the circular backplate sheet from a face of the backplate sheet to a posterior surface of the backplate sheet. The methods include forming a plurality of spaced apart elongated slits elongated in a radial outward direction. The plurality of spaced apart elongated slits formed to extend through the circular backplate sheet from the face of the backplate to the posterior of the backplate, the plurality of spaced apart elongated slits formed through the circular backplate sheet such that the plurality of spaced apart elongated slits encircles the central aperture. The methods include bending the backplate sheet into a dome shape.

In some embodiments, forming the central aperture and the plurality of spaced apart elongated slits comprises electrochemically etching the central aperture and the plurality of spaced apart elongated slits.

In some embodiments, forming the central aperture and the plurality of spaced apart elongated slits comprises laser cutting the central aperture and the plurality of spaced apart elongated slits.

In some embodiments, forming the central aperture and the plurality of spaced apart elongated slits comprises forming the central aperture and the plurality of spaced apart elongated slits with substantially no temperature increase to the backplate sheet.

In some embodiments, bending occurs via a mold.

In some embodiments, the method includes comprising grit blasting the posterior surface of the backplate to increase surface roughness.

In some embodiments, the method includes coloring a face of the backplate sheet via electrochemical anodization.

In some embodiments, the method includes cutting the circular backplate sheet from a titanium sheet.

Various embodiments provide a keratoprosthesis apparatus including a collar-button front plate including a stem extending from a cap portion. The apparatus also includes a circular backplate including a central aperture extending through the backplate from a face of the backplate to a posterior surface of the backplate. The stem extends through the central aperture. The circular backplate has a dome-shape and comprises a plurality of spaced apart elongated slits extending radially outwardly from a central portion of the backplate. The plurality of spaced apart elongated slits surround the central aperture and extend through the backplate from the face of the backplate to the posterior of the backplate.

In some embodiments, the keratoprosthesis apparatus includes a corneal graft coupled to the stem between a cap portion of the collar-button front plate and the backplate.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawing, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Following below are more detailed descriptions of various concepts related to, and exemplary embodiments of, inventive systems, methods and components related to a keratoprosthesis.

Figures 1A, 1B:
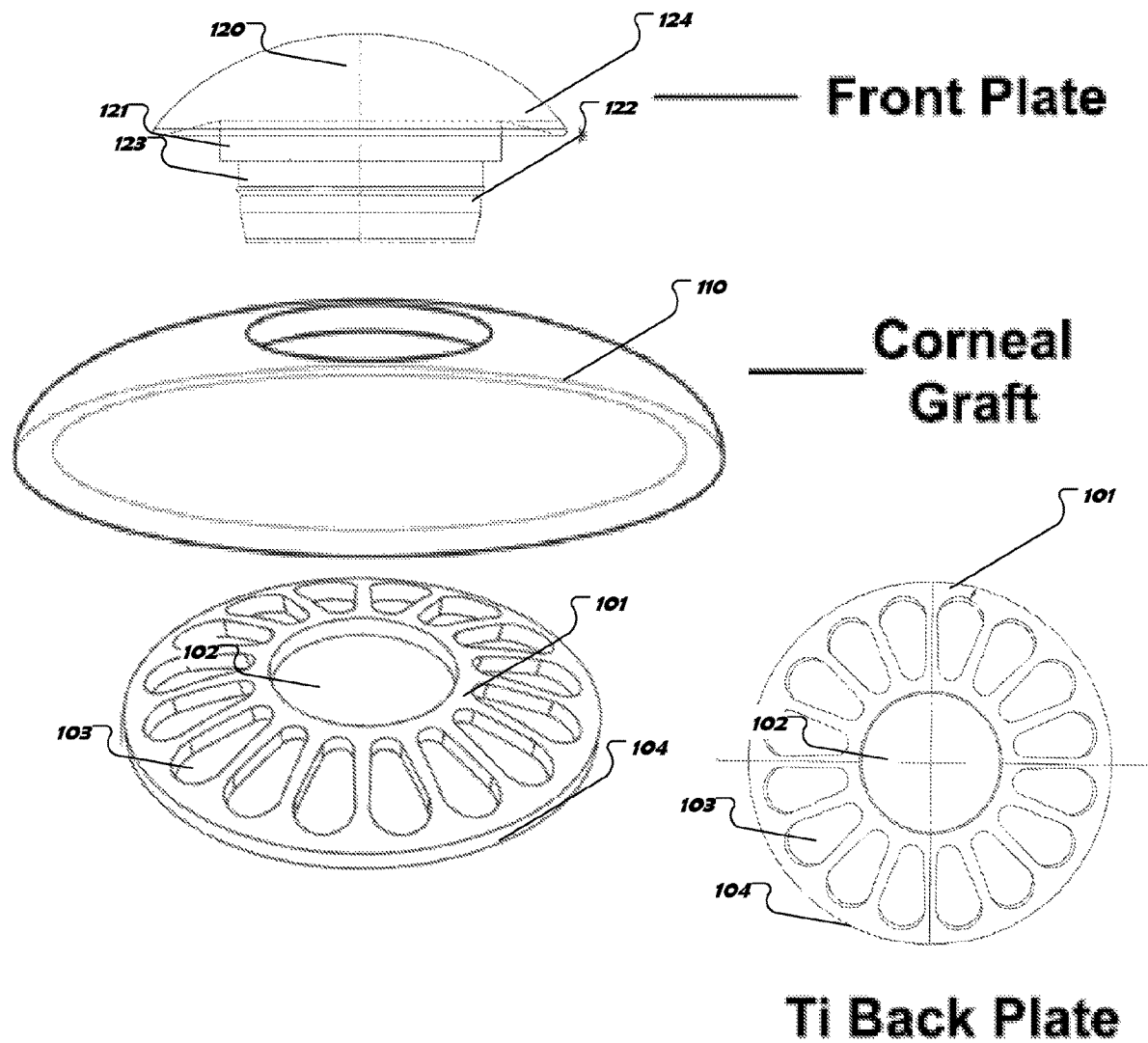
FIG. 1A is an exploded view of a keratoprosthesis 100.
FIG. 1B is a top view of a back plate portion of the keratoprosthesis of FIG. 1.

FIG. 1A is an exploded view of a keratoprosthesis 100. The keratoprosthesis 100 includes a front plate 120 having a stem 121 configured to receive and retain a corneal graft 110, and a backplate 101. The front plate 120 is a collar-button front plate including a cap portion 124. The stem 121 includes a recess 123 configured to receive the backplate 101 and the corneal graft on the stem 121. The corneal graft is configured to be positioned between the front plate 120 and the backplate 101. The stem 121 also includes a cylindrical portion 122 having a cross section corresponding to a central aperture 102 in the backplate 101. The central aperture 102 is shaped to correspond to the shape of portion 123. The backplate 101 and/or the front plate 110 may be composed of titanium in some implementations.

FIG. 1B is a top view of a back plate portion of the keratoprosthesis of FIG. 1. As demonstrated in FIG. 1B, the backplate 101 includes a plurality of spaced apart elongated slits 103. The elongated slits 103 extend radially outwardly from a central portion of the backplate 101 and surround the central aperture 102. The elongated slits 103 widen along their respective longitudinal axes from the central portion of the backplate to an outer circumferential edge 104 of the circular backplate 101. The elongated slits 103 assist with uniformly distributing stresses experienced by the backplate 101 during formation, and in particular during a bending phase discussed further herein. The elongated slits 103 have an appearance that closely corresponds with the appearance of the iris. The elongated slits also provide increased space for aqueous humor penetration to the corneal graft 110.

Figure 2A:
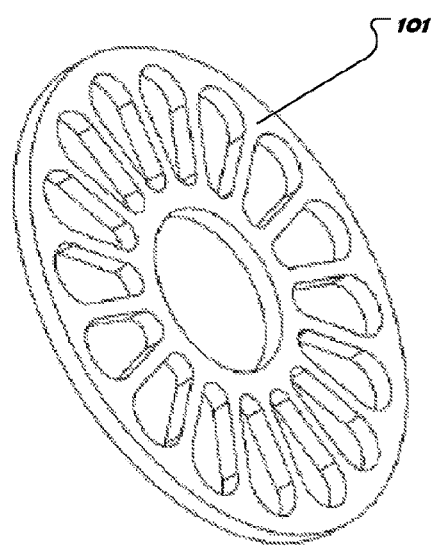
FIGS. 2A and 2B are views of the back plate portion of the keratoprosthesis of FIGS. 1A and 1B before being bent into a curve.
Figure 2B:
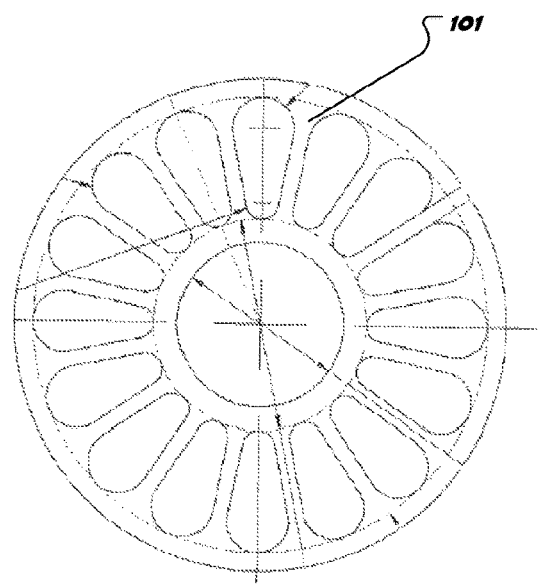
Figure 3:
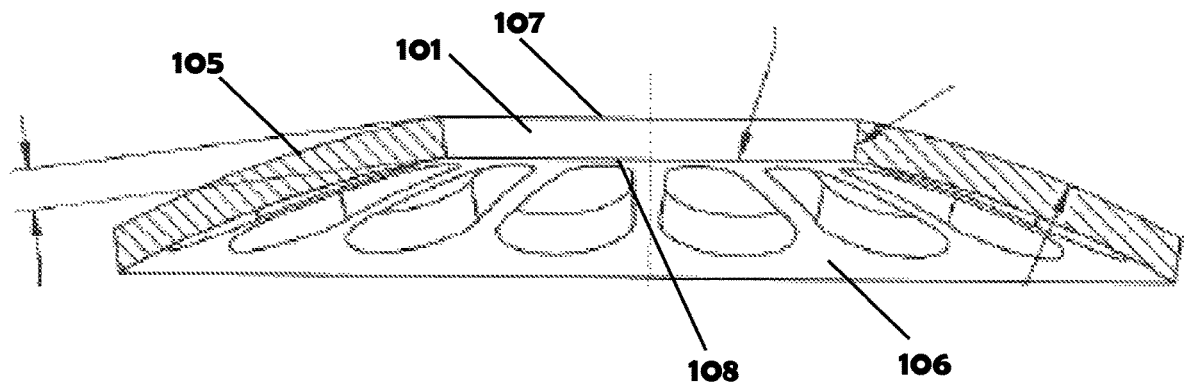
FIG. 3 is side cross sectional view of the back plate portion of the keratoprosthesis of FIG. 1A and FIG. 1B.

FIGS. 2A and 2B are views of the back plate portion of the keratoprosthesis of FIGS. 1A and 1B before being bent into a curve and FIG. 3 is side cross sectional view of the back plate portion of the keratoprosthesis of FIGS. 1A and 1B. As discussed in further detail below, the backplate 101 has a flattened geometry before it is bent to have a particular curvature. As demonstrated in FIG. 1A and FIG. 3, the backplate 101 is dome-shaped after it has undergone a bending process and includes a face 105 and a posterior surface 106. The backplate 101 includes a first edge 107 and a second edge 108 that allow the backplate 101 to flex when it is pushed on the recess 123 of the stem 121, but return to an unflexed state when not pushed so as to remain tightly engaged with the recess 123 of the stem 121. The first edge 107 is chamfered in certain implementations. The second edge 108 is a squared edge in certain implementations. The second edge 108 has a smaller diameter than the first edge 107 in certain implementations. As discussed in further detail in the Appendix, the posterior surface 106 of the backplate 101 can be modified to roughen the posterior surface 106. As discussed in the Appendix, the posterior surface 106 can be roughened by grit blasting. The roughened posterior surface 106 is configured to inhibit deposition and cell proliferation of on the posterior surface 106 while still permitting and/or promoting cellular functions on the face 104 of the backplate 101 where the corneal graft is engaged. Accordingly, in some implementations the posterior surface 106 can have a rougher surface than the face 104. In some implementations the face 104 may include a polished surface. The backplate 101 may include a linear diameter in the range of 3-12 mm. The backplate 101 may have a radius of curvature of 4-10 mm.

Figure 4:
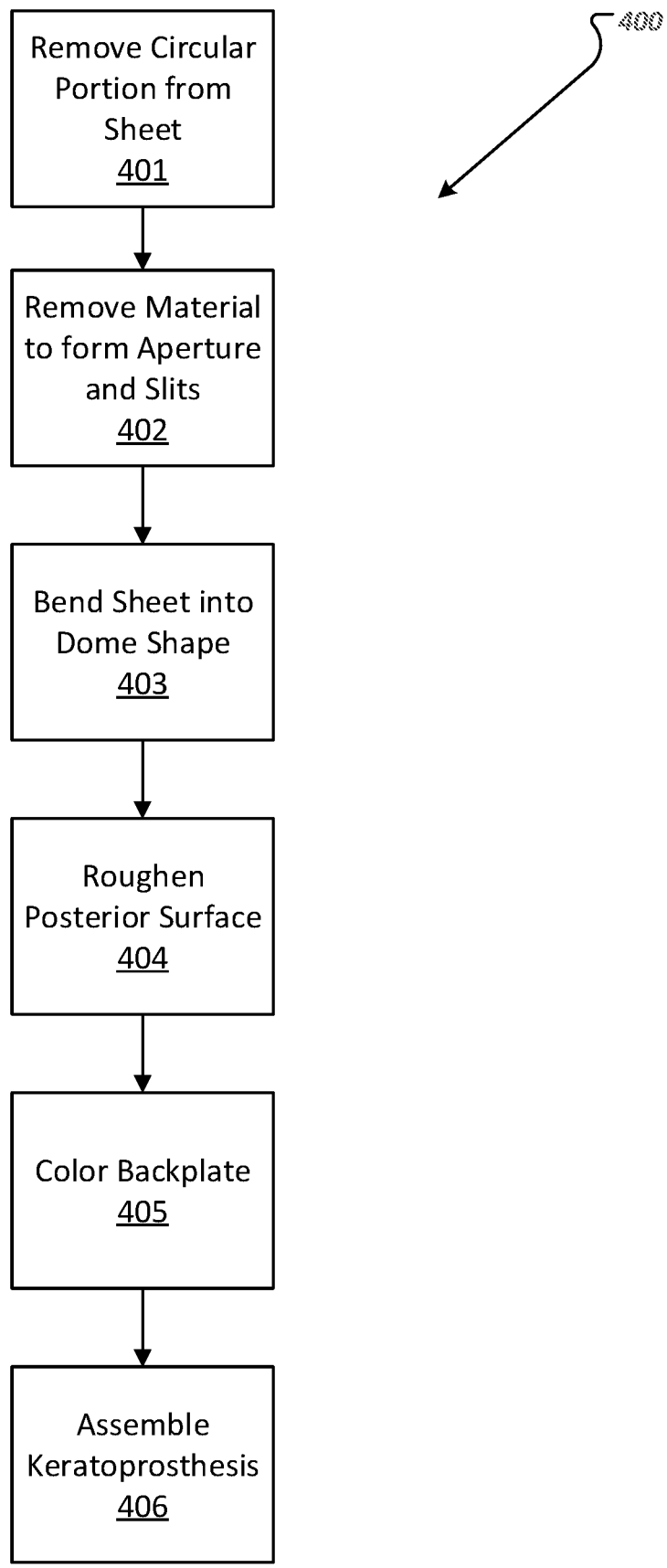
FIG. 4 is a flow diagram of a method of manufacturing the back plate portion of the keratoprosthesis of FIG. 2.

FIG. 4 is a flow diagram of a method 400 of manufacturing the back plate portion 101 of the keratoprosthesis of FIG. 2. In accordance with some embodiments the back plate portion 101 of the keratoprosthesis may be formed from a planar thin titanium sheet. At 401 a circular portion is removed from the planar thin titanium sheet. The circular portion may be removed by cutting. At 402, the central aperture 102 and the elongated slits 103 are formed in the circular portion. In some embodiments, the central aperture 102 and the elongated slits 103 are formed via an electrochemical etching process or photochemical etching. While electrochemical or photochemical etching is generally employed to form the slots, in some implementations other cutting processing may be employed, such as laser cutting and/or other cutting process that generate substantially no temperature increase in the thin sheet. At 403 the planar sheet having the central aperture 102 and the elongated slits 103 formed therein, is bent to have a specific curvature thereby forming the planar thin sheet into a dome shaped component. The bending may be achieved via a mold that the sheet is pressed onto or into. At 404, a posterior surface of the backplate 101 is roughened, in accordance with some implementations and as discussed in further detail in Appendix A. At 405, the backplate 101 is colored, for example via electrochemical anodization, in accordance with some implementations. The backplate 101 may be colored to match the color of a patient's iris, in accordance with some implementations. At 406, the backplate 101 is assembled with one or more of a front plate, such as the front plate 120, and a corneal graft, such as corneal graft 110.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

While various inventive implementations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive implementations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A keratoprosthesis apparatus comprising:
   a circular backplate including a central aperture extending through the backplate from a face of the backplate to a posterior surface of the backplate,
   wherein the circular backplate has a dome shape and comprises a plurality of spaced apart elongated slits extending radially outwardly from a central portion of the backplate surrounding the central aperture and extending through the backplate from the face of the backplate to the posterior surface of the backplate,
   wherein the elongated slits widen along their respective longitudinal axes from the central aperture of the backplate to an outer circumferential edge of the backplate, and
   wherein each elongated slit comprises a portion of a circle at each end of the slit, and wherein the portion of a circle adjacent to the outer circumferential edge has a larger radius of curvature than the portion of a circle adjacent to the central aperture.

2. The apparatus according to claim 1, wherein the face of the backplate is colored to match a color of a patient's iris.

3. The apparatus according to claim 1, wherein the circular backplate is composed of titanium.

4. The apparatus according to claim 1, wherein the posterior surface has a greater roughness than the face.

5. The apparatus according to claim 4, wherein the face is polished.

6. A method of manufacturing a keratoprosthesis apparatus comprising:
   forming a central aperture through a circular backplate sheet to extend through the circular backplate sheet from a face of the backplate sheet to a posterior surface of the backplate sheet;
   forming a plurality of spaced apart elongated slits elongated in a radial outward direction, wherein the plurality of spaced apart elongated slits are formed:
      to extend through the circular backplate sheet from the face of the backplate to the posterior surface of the backplate;
      through the circular backplate sheet such that the plurality of spaced apart elongated slits encircle the central apertures;
      to widen along their respective longitudinal axes from the central aperture of the backplate to an outer circumferential edge of the backplate, and
      to comprise a portion of a circle at each end of the elongated slit and wherein the portion of a circle adjacent to the outer circumferential edge has a larger radius of curvature than the portion of a circle adjacent to the central aperture; and
   bending the backplate sheet into a dome shape.

7. The method according to claim 6, wherein forming the central aperture and the plurality of spaced apart elongated slits comprises electrochemically etching the central aperture and the plurality of spaced apart elongated slits.

8. The method according to claim 6, wherein forming the central aperture and the plurality of spaced apart elongated slits comprises laser cutting the central aperture and the plurality of spaced apart elongated slits.

9. The method according to claim 6, wherein forming the central aperture and the plurality of spaced apart elongated slits comprises forming the central aperture and the plurality of spaced apart elongated slits with substantially no temperature increase to the backplate sheet.

10. The method according to claim 6, wherein bending occurs via a mold.

11. The method according to claim 6, further comprising grit blasting the posterior surface of the backplate to increase surface roughness.

12. The method according to claim 6, further comprising coloring a face of the backplate sheet via electrochemical anodization.

13. The method according to claim 6, further comprising cutting the circular backplate sheet from a titanium sheet.

14. A keratoprosthesis apparatus comprising:
a collar-button front plate including a stem extending from a cap portion; and
a circular backplate including a central aperture extending through the backplate from a face of the backplate to a posterior surface of the backplate,
wherein the stem extends through the central aperture,
wherein the circular backplate has a dome-shape and comprises a plurality of spaced apart elongated slits extending radially outwardly from a central portion of the backplate surrounding the central aperture and extending through the backplate from the face of the backplate to the posterior surface of the backplate,
wherein the elongated slits widen along their respective longitudinal axes from the central aperture of the backplate to an outer circumferential edge of the backplate, and
wherein each elongated slit comprises a portion of a circle at each end of the slit, and wherein the portion of a circle adjacent to the outer circumferential edge has a larger radius of curvature than the portion of a circle adjacent to the central aperture.

15. The keratoprosthesis apparatus according to claim 14, further comprising a corneal graft coupled to the stem between the cap portion of the collar-button front plate and the backplate.

16. The keratoprosthesis apparatus according to claim 14, wherein the face of the backplate is colored to match a color of a patient's iris.

* * * * *

UNITED STATES PATENT AND TRADEMARK OFFICE
CERTIFICATE OF CORRECTION

PATENT NO. : 10,939,993 B2
APPLICATION NO. : 16/091672
DATED : March 9, 2021
INVENTOR(S) : James Chodosh, Eleftherios Paschalis Ilios and John Graney Page 1 of 1

It is certified that error appears in the above-identified patent and that said Letters Patent is hereby corrected as shown below:

In the Claims

In Column 6, Line 45, Claim 6, delete "apertures;" and insert -- aperture; --

Signed and Sealed this
Eighth Day of June, 2021

Drew Hirshfeld
*Performing the Functions and Duties of the
Under Secretary of Commerce for Intellectual Property and
Director of the United States Patent and Trademark Office*